US00PP37327P2

(12) United States Plant Patent
Korlipara

(10) Patent No.: US PP37,327 P2
(45) Date of Patent: Mar. 10, 2026

(54) ***ECHINACEA* PLANT NAMED 'TNECHFT'**

(50) Latin Name: ***Echinacea* spp.**
Varietal Denomination: TNECHFT

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 19/186,398

(22) Filed: Apr. 22, 2025

(51) Int. Cl.
*A01H 5/02* (2018.01)

(52) U.S. Cl.
USPC ..... Plt./428

(58) Field of Classification Search
USPC ..... Plt./428
CPC ..... A01H 5/02; A01H 5/00; A01H 6/1448; A01H 6/14
See application file for complete search history.

(56) References Cited

PUBLICATIONS

BFG Supply Terra Nova Nurseries, Inc. 2025 Program, retrieved on Jun. 4, 2025 at https://www.bfgsupply.com/media/9166/2024-2025-terra-nova-product-program.pdf, 12 pp. (Year: 2025).*
Farwest 2024 New Varieties Showcase winners!, retrieved on Jun. 4, 2025 at https://farwestshow.com/new-varieties-showcase/, 8 pp. (Year: 2025).*
Floral Daily Photo report: Cultivate 2024, retrieved on Jun. 4, 2025 at https://www.floraldaily.com/article/9646332/photo-report-cultivate-2024/, 4 pp. (Year: 2024).*
McDaniel 2024 Farwest Show registration now open, retrieved on Jun. 4, 2025 at https://www.nurserymag.com/news/2024-farwest-show-registration/, 4 pp. (Year: 2024).*
Priva Cultivate24 retrieved on Jun. 4, 2025 at https://www.priva.com/events/cultivate24#:~:text=Priva%20at%20Cultivate'24%20from,anyone%20in%20the%20green%20industry, 3 pp. (Year: 2025).*

* cited by examiner

*Primary Examiner* — June Hwu
(74) *Attorney, Agent, or Firm* — Klarquist Sparkman, LLP

(57) ABSTRACT

A new and distinct *Echinacea* cultivar named 'TNECHFT' distinguished by its large number of medium inflorescences starting in the first season, long bloom time with excellent rebloom, upright and compact habit, white tipped rose-pink ray florets surrounding dark cones, horizontally held ray florets, strong upright stems, and excellent vigor from spring through fall.

2 Drawing Sheets

Latin name of the genus and species of the plant claimed: *Echinacea* spp.

Variety designation: 'TNECHFT'.

BACKGROUND

The present application relates to a new and distinct cultivar of *Echinacea* given the cultivar name 'TNECHFT'. The cultivar is also known by its trade name, FRENCH TIPS™. *Echinacea* is in the family Asteraceae. The new cultivar is part of a planned breeding program for a garden series with compact habits and profuse inflorescences. The parents of this selection are unnamed, proprietary interspecific hybrids E-2110-1 x E-2009. Neither parent still exists.

SUMMARY

The new *Echinacea* cultivar 'TNECHFT' is distinguished from other *Echinacea* cultivars due to the following unique combination of characteristics:

1. Very large number of medium inflorescences, over 100, starting in the first season.
2. Very long bloom time with excellent rebloom.
3. Very upright, compact habit.
4. Rose-pink ray florets with white tips surrounding dark cones.

5. Ray florets held horizontally.
6. Strong upright stems.
7. Excellent vigor from spring through fall.

Compared to *Echinacea* 'TNECHKR' (U.S. Plant Pat. No. 28,768), the new cultivar is distinguished at least by its more rose-pink and softer colored ray florets with white tips and greater number of disc florets.

The new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oregon, shows that the characteristics described herein come true to form, are firmly fixed, and are established and transmitted through succeeding propagations.

The new cultivar has not been evaluated under all possible environmental conditions and certain characteristics may change with changing environmental conditions (such as photoperiod, temperature, moisture, soil conditions, nutrient availability, or other factors). The phenotype may change with variations in environment without a change in the genotype of the plant.

Figure 1:
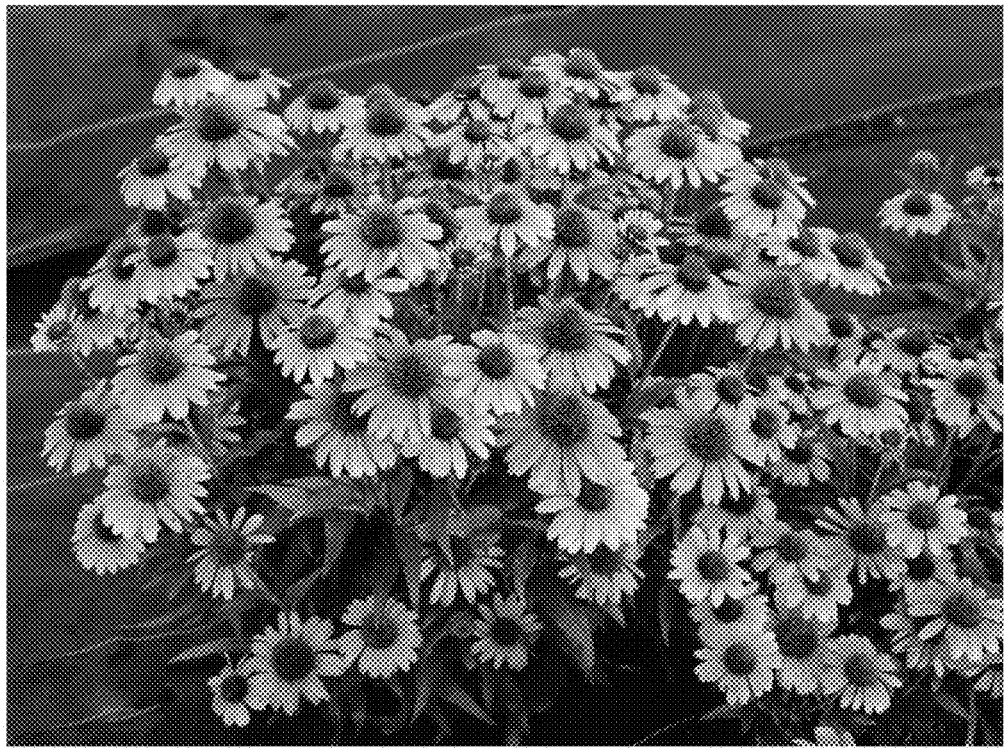
FIG. 1 shows a 2-year-old 'TNECHFT' plant growing in the trial field in full sun on Jul. 22, 2024, in Canby, Oregon.
Figure 2:
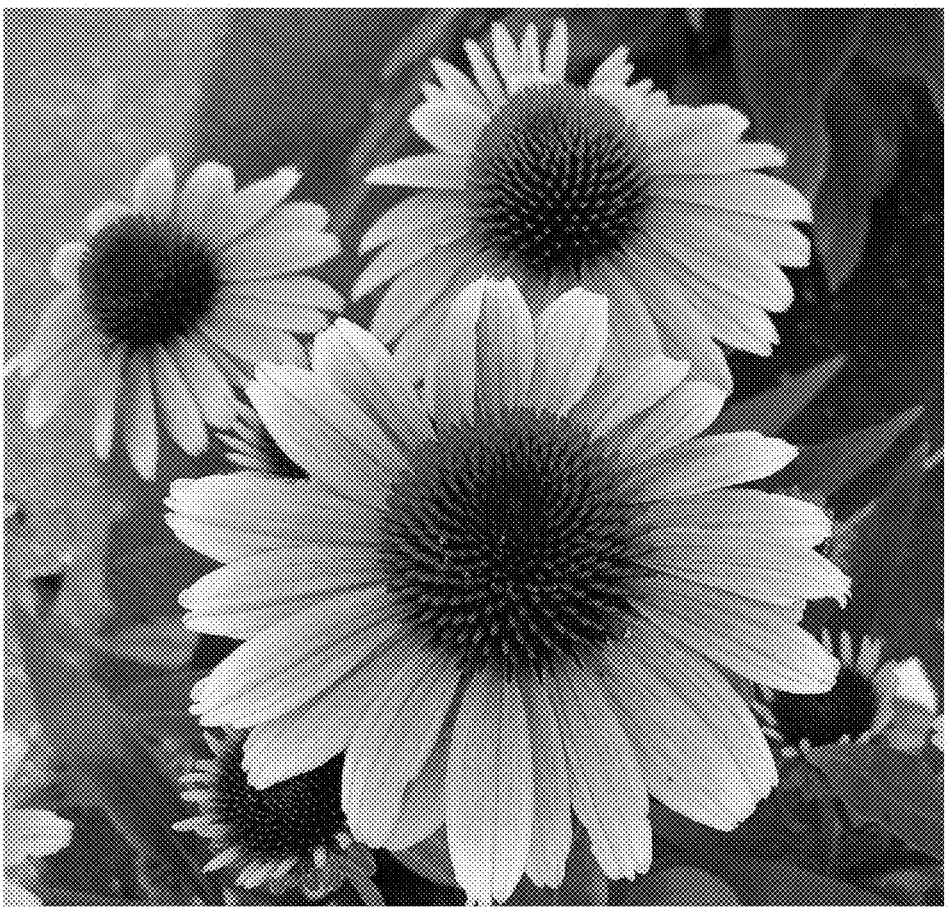
FIG. 2 shows a closeup of individual flowers of 'TNECHFT'.

The color photographs show typical specimens of the new cultivar and depict the color as nearly true as is reasonably possible. It should be noted that colors may vary, for example due to lighting conditions at the time the photograph is taken. Therefore, color characteristics of this new cultivar should be determined with reference to the observations described herein, rather than from the photograph alone.

DETAILED PLANT DESCRIPTION

The following is a detailed description of the new *Echinacea* cultivar based on observations of 9-month-old specimens growing in a trial bed in full sun in Canby, Oregon. Canby is Zone 8 on the USDA Hardiness map. Temperatures range from a high of 95° F. in August to an average of 32° F. in January. Normal rainfall in Canby is 42.8 inches per year.

Color descriptions and other terminology are used in accordance with their ordinary dictionary descriptions, unless the context clearly indicates otherwise. Color descriptions used herein are made with reference to *The Royal Horticultural Society Colour Chart,* 5$^{th}$ edition, 2007.

Plant:

*Type*.—Herbaceous perennial.

*Hardiness*.—USDA Zone 4 to 9.

*Size*.—Grows to 75 cm wide and 53 cm tall to top of inflorescences.

*Form*.—Basal clump with 15 to 20 stems from the base.

*Vigor*.—Excellent from spring through fall.

*Roots*.—Fibrous, with many downward growing and few laterals, ivory to cream in color, yellow-white 158D, roots develop easily from cuttings from the crown.

Leaf (basal):

*Type*.—Simple.

*Arrangement*.—Rosette.

*Shape*.—Lanceolate.

*Blade size*.—Grows to 13 cm long and 4 cm wide.

*Margins*.—Entire to minorly dentate and slightly undulate.

*Apex*.—Acute.

*Base*.—Attenuate.

*Surface texture*.—Strigose on both sides.

*Venation*.—Arcuate to pinnate, yellow-green 145D on both sides.

*Color*.—Topside green N137B, bottom side closest to yellow-green 147B.

*Petiole description*.—Clasping, grows to 9 cm long and 3 mm wide, scabrous, edges slightly to entirely winged and slightly keeled, topside yellow-green 145C with red-purple 61B at base, bottom side closest to yellow-green 145C tinted red-purple 61B at base.

Leaf (stem):

*Type*.—Simple.

*Shape*.—Lanceolate.

*Arrangement*.—Alternate.

*Blade size*.—Grows to 13 cm long and 3 cm wide.

*Margins*.—Mostly entire.

*Apex*.—Acute.

*Base*.—Attenuate.

*Surface texture*.—Strigose on both sides.

*Rugosity*.—Weak.

*Venation*.—Arcuate to pinnate, Yellow Green 149D on top side yellow green 145D on bottom.

*Color*.—Topside Green N137B, bottom side closest to Yellow Green 147B.

*Petiole description*.—Clasping, grows to 8 cm long and 3 mm wide, scabrous, edges slightly to entirely winged and slightly keeled, topside Yellow Green 145C, bottom side Yellow Green 145B.

Inflorescence:

*Size*.—Grows to 10 cm wide and 3 cm deep as disc enlarges.

*Type*.—Composite on terminal stalked heads.

*Form*.—Ray florets held horizontally, reflexing somewhat in very old flowers, mature disc is conic.

*Immature inflorescence* (*bud*).—Size — 2 cm wide and 1-1.5 cm deep. Description — ray florets held upright at a 70 degrees angle from vertical and rolled up so only the back color shows. Color — yellow-green 150A at tip to red-purple 59B at base. Disc closest to gray-brown N199C with green 143B at center.

*Ray florets* (*without pistil or stamen*).—Number — approximately 15-27. Size — grows to 47 mm long and 13 mm wide. Shape — oblanceolate with the tip two-to-three-toothed (each acute). Margins — entire. Base — attenuate. Texture — glabrous on both sides. Color — topside of fully open florets color at tip is closest to white N155C fading through red-purple 70B and 70C in the middle to red-purple 64C at the base. Bottom side of fully open florets color is yellow-green 149C at the tip fading to red-purple 70C at the base. Pedicel — absent, ray florets sessile, joined directly to receptacle.

*Disc*.—Shape — flat becoming conic, becoming 40 mm deep and 45 mm wide with maturity.

*Disc florets*.—Number — about 472, each with 1 pistil and 5 stamen. Size — grows to 10 mm long and 2 mm wide, each with one persistent, very stiff linear palea that measures approximately (11.5 mm long; top 0.5 mm is orange N25D, remaining 11 mm is yellow-green 146C fading to yellow-green 146D at base). Pedicel — absent, disc florets sessile, joined directly to receptacle. Corolla — 7 mm long and 3 mm wide, tubular, 5 lobed, glabrous and glossy, grayed-green 195A at the base blending to green 139D on the lobes. Pistil: Length — 10 mm long. Ovary — 2 mm long, white 155A. Style — 5 mm long, white NN155C at base fading to gray-purple 187D. Stigma — two branched stigma spreading 3 mm wide, puberulent, greyed-purple 187A. Stamen: Length — 6 mm long. Filaments — 2 mm long and white 155C. Anthers — 4 mm long and brown N200A. Pollen Color — yellow-orange 21A.

*Involucral bracts*.—In 4 leafy series, area grows to 35 mm wide and 17 mm deep, lobes lanceolate in shape, reflexed, grow to 17 mm long and 3 mm wide, green 137B, margins strigose, tip acute, strigose on both sides.

*Receptacle*.—Size — grows to 15 mm wide and 23 mm deep. Color — White NN155B quickly oxidizes to grayed-orange 134D.

*Flowering stem*.—Size — grows to 54 cm tall from the base of the plant to the terminal inflorescence.

Branching — unbranched to branched. Inflorescences per Stem — 1 to 5. Diameter — up to 9 mm wide near the inflorescence. Texture — strigose. Color — yellow-green 145B in the shade, tinted red-purple 61B in the sun.

*Bloom period*.—June through October in Canby, Oregon.

*Fragrance*.—Moderate, pleasant.

*Lastingness*.—Each inflorescence lasts about two weeks in Canby, Oregon.

Seed:

*Shape*.—Oval.

*Size*.—3 mm long and 1-2 mm wide.

*Color*.—Brown 200C.

Pest and disease tolerance: Eriophyid mites have been observed on plants grown under commercial conditions in Canby, Oregon. There are no known resistances.

I claim:

1. A new and distinct *Echinacea* plant named 'TNECHFT' substantially as illustrated and described herein.

* * * * *